(12) United States Patent
Jacquin et al.

(10) Patent No.: US 8,845,787 B2
(45) Date of Patent: *Sep. 30, 2014

(54) ABSORBENT SOLUTION BASED ON N, N, N', N'-TETRAMETHYLHEXANE-1,6-DIAMINE AND ON A PARTICULAR AMINE COMPRISING PRIMARY OR SECONDARY AMINE FUNCTIONS AND METHOD FOR REMOVING ACID COMPOUNDS FROM A GASEOUS EFFLUENT

(75) Inventors: Marc Jacquin, Lyons (FR); Julien Grandjean, Lyons (FR); Thierry Huard, Saint Symphorien d'Ozon (FR)

(73) Assignee: IFP Energies Nouvelles, Rueil-Malmaison Cedex (FR)

( * ) Notice: Subject to any disclaimer, the term of this patent is extended or adjusted under 35 U.S.C. 154(b) by 150 days.

This patent is subject to a terminal disclaimer.

(21) Appl. No.: 13/056,507

(22) PCT Filed: Jul. 21, 2009

(86) PCT No.: PCT/FR2009/000901
§ 371 (c)(1),
(2), (4) Date: Apr. 18, 2011

(87) PCT Pub. No.: WO2010/012883
PCT Pub. Date: Feb. 4, 2010

(65) Prior Publication Data
US 2011/0185901 A1 Aug. 4, 2011

(30) Foreign Application Priority Data
Jul. 28, 2008 (FR) ...................... 08 04304

(51) Int. Cl.
| | | |
|---|---|---|
| *B01D 53/14* | (2006.01) | |
| *C10L 3/10* | (2006.01) | |
| *C07C 211/12* | (2006.01) | |
| *C07C 215/08* | (2006.01) | |
| *B01D 53/62* | (2006.01) | |
| *B01D 53/77* | (2006.01) | |

(52) U.S. Cl.
CPC ............ *B01D 53/62* (2013.01); *B01D 2258/05* (2013.01); *B01D 2257/504* (2013.01); *C10L 3/102* (2013.01); *B01D 53/77* (2013.01); *Y02C 10/04* (2013.01); *B01D 2251/80* (2013.01); *Y02C 10/06* (2013.01); *B01D 2258/06* (2013.01); *B01D 2257/30* (2013.01); *C07C 211/12* (2013.01); *C07C 215/08* (2013.01); *C10L 3/10* (2013.01); *B01D 53/1493* (2013.01)
USPC .................. 95/173; 95/174; 95/181; 95/183; 95/235; 95/236; 252/184; 423/228

(58) Field of Classification Search
USPC ...................... 95/236; 423/228; 252/60, 184
See application file for complete search history.

(56) References Cited

U.S. PATENT DOCUMENTS

| 6,852,144 | B1 | 2/2005 | Wagner et al. |
| 7,323,100 | B2 * | 1/2008 | Espinoza et al. ........... 208/111.3 |
| 2006/0011512 | A1 | 1/2006 | Espinoza |

FOREIGN PATENT DOCUMENTS

| EP | 0 365 850 | 5/1990 |
| EP | 1 775 633 | 4/2007 |

(Continued)

OTHER PUBLICATIONS

Arthur Kohl, "Gas Purification" Fifth Edition, Chapter 14, Mixed Physical/Chemical Solvent Processes, 1997, Gulf Publishing Company.

*Primary Examiner* — Duane Smith
*Assistant Examiner* — Cabrena Holecek
(74) *Attorney, Agent, or Firm* — Antonelli, Terry, Stout & Kraus, LLP.

(57) ABSTRACT

Acid compounds are removed from a gaseous effluent in an absorption method using an aqueous solution of N,N,N',N'-tetramethylhexane-1,6-diamine formulated with a particular primary or secondary amine, allowing to obtain a single-phase absorbent solution under the absorption conditions of acid gases such as $CO_2$.
The method is advantageously applied to the treatment of natural gas and of gas of industrial origin.

13 Claims, 2 Drawing Sheets

(56) References Cited

FOREIGN PATENT DOCUMENTS

| FR | 2 820 430 | 8/2002 | | | |
|----|-----------|--------|---|---|---|
| FR | 2 898 284 | | 9/2007 | | |
| FR | 2898284 | * | 9/2007 | ............ | B01D 53/14 |
| FR | 2900841 A1 | * | 11/2007 | ............ | B01D 53/14 |

* cited by examiner

ABSORBENT SOLUTION BASED ON N, N, N', N'-TETRAMETHYLHEXANE-1,6-DIAMINE AND ON A PARTICULAR AMINE COMPRISING PRIMARY OR SECONDARY AMINE FUNCTIONS AND METHOD FOR REMOVING ACID COMPOUNDS FROM A GASEOUS EFFLUENT

FIELD OF THE INVENTION

The present invention relates to the absorption of acid compounds ($H_2S$, $CO_2$, COS, $CS_2$, mercaptans, etc.) contained in a gas, by means of an absorbent aqueous solution comprising the combination of a particular tertiary diamine, N,N,N',N'-tetramethylhexane-1,6-diamine, and of a particular primary or secondary amine, allowing to obtain a single-phase absorbent solution under the absorption conditions of acid gases such as $CO_2$. The invention is advantageously applied to the treatment of natural gas and of gas of industrial origin.

BACKGROUND OF THE INVENTION

Treatment of Gas of Industrial Origin

The nature of the gaseous effluents that can be treated is varied, non-limitative examples thereof are syngas, combustion fumes, refinery gas, Claus tail gases, biomass fermentation gases, cement plant gases and blast furnace gases.

All these gases contain acid compounds such as carbon dioxide ($CO_2$), hydrogen sulfide ($H_2S$), carbon oxysulfide (COS), carbon disulfide ($CS_2$) and mercaptans (RSH), mainly methylmercaptan ($CH_3SH$), ethylmercaptan ($CH_3CH_2SH$) and propylmercaptans ($CH_3CH_2CH_2SH$).

For example, in the case of combustion fumes, $CO_2$ is the acid compound to be removed. In fact, carbon dioxide is one of the greenhouse gases widely produced by human activities and it has a direct impact on atmospheric pollution. In order to reduce the amounts of carbon dioxide discharged to the atmosphere, it is possible to capture the $CO_2$ contained in a gaseous effluent.

Treatment of Natural Gas

In the case of natural gas, three main treating operations are considered: deacidizing, dehydration and stripping. The goal of the first stage, deacidizing, is to remove acid compounds such as carbon dioxide ($CO_2$), as well as hydrogen sulfide ($H_2S$), carbon oxysulfide (COS), carbon disulfide ($CS_2$) and mercaptans (RSH), mainly methylmercaptan ($CH_3SH$), ethylmercaptan ($CH_3CH_2SH$) and propylmercaptans ($CH_3CH_2CH_2SH$). The specifications generally admitted for deacidized gas are 2% $CO_2$, or even 50 ppm $CO_2$, the natural gas being thereafter subjected to liquefaction; 4 ppm $H_2S$ and 10 to 50 ppm volume of total sulfur. The dehydration stage then allows to control the water content of the deacidized gas in relation to the transport specifications. Finally, the natural gas stripping stage allows to guarantee the dew point of the hydrocarbons in the natural gas, here again according to transport specifications.

Deacidizing is therefore often carried out first, notably in order to remove the toxic acid gases such as $H_2S$ in the first stage of the chain of processes and thus to avoid pollution of the various unit operations by these acid compounds, notably the dehydration section, the condensation and separation section intended for the heavier hydrocarbons.

Acid Compounds Removal by Absorption

Deacidizing gaseous effluents, such as natural gas and combustion fumes for example, as well as syngas, refinery gas, Claus tail gas, biomass fermentation gas, cement plant gas and blast furnace gas, is generally carried out by washing with an absorbent solution. The absorbent solution allows to absorb the acid compounds present in the gaseous effluent (notably $H_2S$, mercaptans, $CO_2$, COS, $CS_2$).

The solvents commonly used today are aqueous solutions of primary, secondary or tertiary alkanolamine, in combination with an optional physical solvent. Document FR-2,820,430, which provides gaseous effluent deacidizing methods, can be mentioned by way of example. U.S. Pat. No. 6,852,144, which describes a method of removing acid compounds from hydrocarbons, can also be mentioned. The method uses a water-methyldiethanolamine or water-triethanolamine absorbent solution containing a high proportion of a compound belonging to the following group: piperazine and/or methylpiperazine and/or morpholine.

For example, in the case of $CO_2$ capture, the absorbed $CO_2$ reacts with the amine present in solution according to a reversible exothermic reaction known to the person skilled in the art and leading to the formation of hydrogen carbonates, carbonates and/or carbamates, allowing removal of the $CO_2$ from the gas to be treated. Similarly, for the removal of $H_2S$ from the gas to be treated, the absorbed $H_2S$ reacts with the amine present in solution according to a reversible exothermic reaction known to the person skilled in the art and leading to the formation of hydrosulfide.

Another essential aspect of the operations for treating industrial gas or fumes by a solvent is the separation agent regeneration stage. Regeneration through expansion and/or distillation and/or entrainment by a vaporized gas referred to as "stripping gas" is generally provided depending on the absorption type (physical and/or chemical).

One of the main limitations of the solvents commonly used today is the necessity of using high absorbent solution flow rates, which leads to a high energy consumption for solvent regeneration, as well as substantial equipment sizes (columns, pumps, etc.). This is particularly true in cases where the acid gas partial pressure is low. For example, for a 30 wt. % monoethanolamine aqueous solution used for post-combustion $CO_2$ capture in a thermal power plant fume, where the $CO_2$ partial pressure is of the order of 0.1 bar, the regeneration energy represents approximately 3.9 GJ per ton of $CO_2$ captured (reference case, CASTOR project, post-combustion capture pilot unit of the Esbjerg power plant). Such an energy consumption represents a considerable operating cost for the $CO_2$ capture method.

In general terms, for treating acid effluents that comprise acid compounds such as $H_2S$, mercaptans, $CO_2$, COS, $SO_2$, $CS_2$ for example, using amine-based compounds is interesting because of their ease of use in aqueous solution. However, when deacidizing these effluents, the absorbent solution may degrade, either through thermal degradation or through side reaction with the acid gases to be captured, and with other compounds contained in the effluents, such as oxygen, the SOx and the NOx contained in industrial fumes for example. These degradation reactions affect the proper functioning of the method: solvent efficiency decrease, corrosion, foaming, etc. Due to these degradations, it is necessary to carry out solvent purification by distillation and/or ion exchange and to provide make-up amine. By way of example, the make-up amine added in a post-combustion $CO_2$ capture method using a 30 wt. % monoethanolamine absorbent solution represents 1.4 kg amine per ton of $CO_2$ captured, which significantly increases the operating cost of a capture unit.

Finally, these degradation reactions limit the operating conditions of the method, notably the temperature at which solvent regeneration is conducted. By way of example, increasing the regenerator temperature by 10° C. doubles the thermal degradation rate of monoethanolamine. The regeneration of alkanolamine aqueous solutions such as monoethanolamine is therefore carried out at regenerator bottom temperatures of the order of 110° C., or even 130° C. for more stable amines such as methyldiethanolamine. As a result of these regenerator bottom temperatures, the acid gases ($H_2S$, $CO_2$, COS, $CS_2$ etc.) are obtained at moderate pressures ranging from 1 to 3 bars. Depending on the nature of the regenerated acid gas and on applications, the acid gas can be sent to a treating unit or it can be compressed in order to be reinjected and sequestered.

It is difficult to find a stable absorbent compound allowing to remove acid compounds in any effluent type and allowing the deacidizing method to operate at a lesser cost. The applicant has found that N,N,N',N'-tetramethylhexane-1,6-diamine or TMHDA, alone or in admixture with some wt. % of primary or secondary amines, is of great interest in all the gaseous effluent treatment methods intended for acid compounds removal.

However, most absorbent aqueous solutions comprising N,N,N',N'-tetramethylhexane-1,6-diamine or TMHDA, alone or in admixture with some wt. % of primary or secondary amines, exhibit a liquid-liquid phase separation upon $CO_2$ absorption under the absorber conditions. In form of two separate phases, the stream of acid compounds transferred from the gas to the absorbent solution would be highly impacted and the column height would have to be adjusted accordingly. This phenomenon therefore poses serious implementation problems and, considering the complexity of the system, it is difficult to model. Surprisingly, the applicant has found that adding some wt. % of particular primary or secondary amines to an aqueous solution of N,N,N',N'-tetramethylhexane-1,6-diamine allows to obtain a single-phase absorbent solution under the conditions of absorption of acid gases such as $CO_2$.

DESCRIPTION OF THE INVENTION

The object of the present invention thus is to overcome one or more of the drawbacks of the prior art by providing a method for removing acid compounds such as $CO_2$, $H_2S$, COS, $CS_2$ and mercaptans from a gas using the combination of two specific amines whose properties allow, while keeping a single-phase absorbent solution under the conditions of absorption of the acid gases, to limit the flow rate of absorbent solution to be used, notably at a low acid gas partial pressure, and which exhibit a very high stability.

A first object of the invention is an absorbent aqueous solution comprising the combination of N,N,N',N'-tetramethylhexane-1,6-diamine of formula (I) and of an activator of formula (II) or (III).

The present invention also relates to a method of removing the acid compounds contained in a gaseous effluent, such as natural gas and gases of industrial origin, comprising:
an acid compound absorption stage by contacting the effluent with an aqueous solution comprising the N,N,N',N'-tetramethylhexane-1,6-diamine and an activator of formula (II) or (III),
optionally at least one stage of liquid-liquid separation of the solution laden with acid gas after heating, allowing fractionated regeneration of the absorbent solution,
at least one stage of regeneration of the absorbent solution laden with acid compounds.

The invention also relates to the application of said acid compound removal method to the treatment of natural gas or of gas of industrial origin, notably to post-combustion $CO_2$ capture.

SUMMARY OF THE INVENTION

The invention relates to an absorbent solution for absorbing the acid compounds of a gaseous effluent, comprising:
water,
at least one amine of formula (I) (named N,N,N',N'-tetramethylhexane-1,6-diamine or TMHDA)

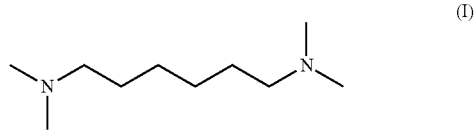

at least one primary or secondary amine of formula (II) or (III).

According to the invention, formula (II) is of the form as follows:

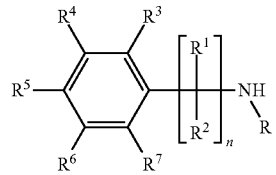

wherein
n=1 or 2, preferably n=1
each group R1, R2, R3, R4, R5, R6, R7 and R is selected independently among one of the elements of the group made up of: a hydrogen atom, an alkyl group with 1 to 2 carbon atoms. According to an embodiment of the molecule of formula (II), group R is independent and it is therefore not linked to any one of groups R1 to R7. According to another embodiment of the molecule of formula (II), group R can be linked by R3 or R7 to the aromatic ring of formula (II), so as to form a heterocycle with 5 to 6 atoms.

According to the invention, formula (III) is of the form as follows:

wherein
R is a linear or branched alkyl group with 4 to 8 carbon atoms,
groups R1 and R2 are selected independently among one of the elements of the group made up of:
a hydrogen atom,
a linear or branched alkyl group with 1 to 4 carbon atoms,
a group

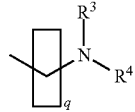

wherein q is 2 or 3, and groups R3, R4 are selected independently among a hydrogen atom or a linear or branched alkyl group with 1 to 4 carbon atoms.

According to an embodiment of the molecule of formula (III), group R is independent and therefore group R is not linked to group R1 or R2. According to another embodiment of the molecule of formula (III), group R can be linked to one of groups R1 or R2 so as to form a heterocycle with 5 or 6 atoms.

Besides, according to an embodiment of the molecule of formula (III), group R3 is independent and it is therefore not linked to group R1 or R2. According to another embodiment of the molecule of formula (III), group R3 can be linked to R1 or R2 so as to form a heterocycle with 5 to 6 atoms.

The absorbent solution advantageously comprises 10 to 90 wt. % N,N,N',N'-tetramethylhexane-1,6-diamine, preferably 20 to 60 wt. % N,N,N',N'-tetramethylhexane-1,6-diamine and more preferably 30 to 50 wt. % N,N,N',N'-tetramethylhexane-1,6-diamine.

The absorbent solution comprises a non-zero proportion, below 50 wt. %, preferably 20 wt. %, of an activating organic compound of formula (II) or (III).

More preferably, the activator is selected from the group made up of:
amines of formula (II):

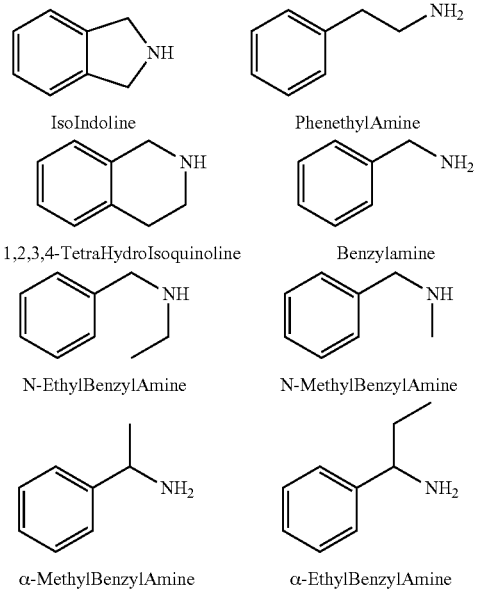

and amines of formula (III):

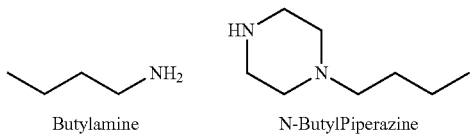

The absorbent solution can comprise a physical solvent.
The absorbent solution can comprise an organic or inorganic solvent.

The invention also relates to a method for removing the acid compounds contained in a gaseous effluent, comprising:
an acid compound absorption stage by contacting the effluent with an absorbent solution according to the invention so as to obtain a gaseous effluent depleted in acid compounds and an absorbent solution laden with acid compounds,
at least one stage of regeneration of the absorbent solution laden with acid compounds.

In an embodiment of the method according to the invention, it is possible to carry out the absorption stage so as to obtain a gaseous effluent depleted in acid compounds and a single-phase absorbent solution laden with acid compounds, the absorption stage being followed by at least one stage of liquid-liquid separation of the two-phase absorbent solution laden with acid compounds obtained after heating the absorbent solution, then by at least one stage of fractionated regeneration of the absorbent solution laden with acid compounds.

Generally, the acid compound absorption stage is carried out at a pressure ranging between 1 and 120 bars, and at a temperature ranging between 30° C. and 100° C.

Considering the high stability of (N,N,N',N'-tetramethylhexane-1,6-diamine), it is possible to regenerate the absorbent solution according to the invention at high temperature in a distillation column. In general, the thermal regeneration stage is conducted at a pressure ranging between 1 and 10 bars, and at a temperature ranging between 100° C. and 180° C. Preferably, regeneration in the distillation column is performed at a temperature ranging between 155° C. and 165° C., and at a pressure ranging between 6 and 8.5 bars if it is desired to reinject the acid gases. Preferably, regeneration in the distillation column is carried out at a temperature ranging between 115° C. and 130° C., and at a pressure ranging between 1.7 and 3 bars in cases where the acid gas is sent to the atmosphere or to a downstream treating process such as a Claus process or a tail gas treating process.

In a variant of the method according to the invention, a first stage of expansion of the absorbent solution laden with acid compounds is carried out before the regeneration stage.

Preferably, a second stage of expansion of the absorbent solution laden with acid compounds is carried out, the second expansion stage being performed after the first expansion stage and before the regeneration stage, the absorbent solution being heated prior to being subjected to the second expansion stage.

The invention also relates to a method according to the invention for natural gas treatment.

The invention also relates to a method according to the invention for treating gases of industrial origin, preferably for $CO_2$ capture.

BRIEF DESCRIPTION OF THE FIGURES

Other features and advantages of the invention will be clear from reading the description hereafter, with reference to the accompanying figures given by way of example.

DETAILED DESCRIPTION

Figure 1:
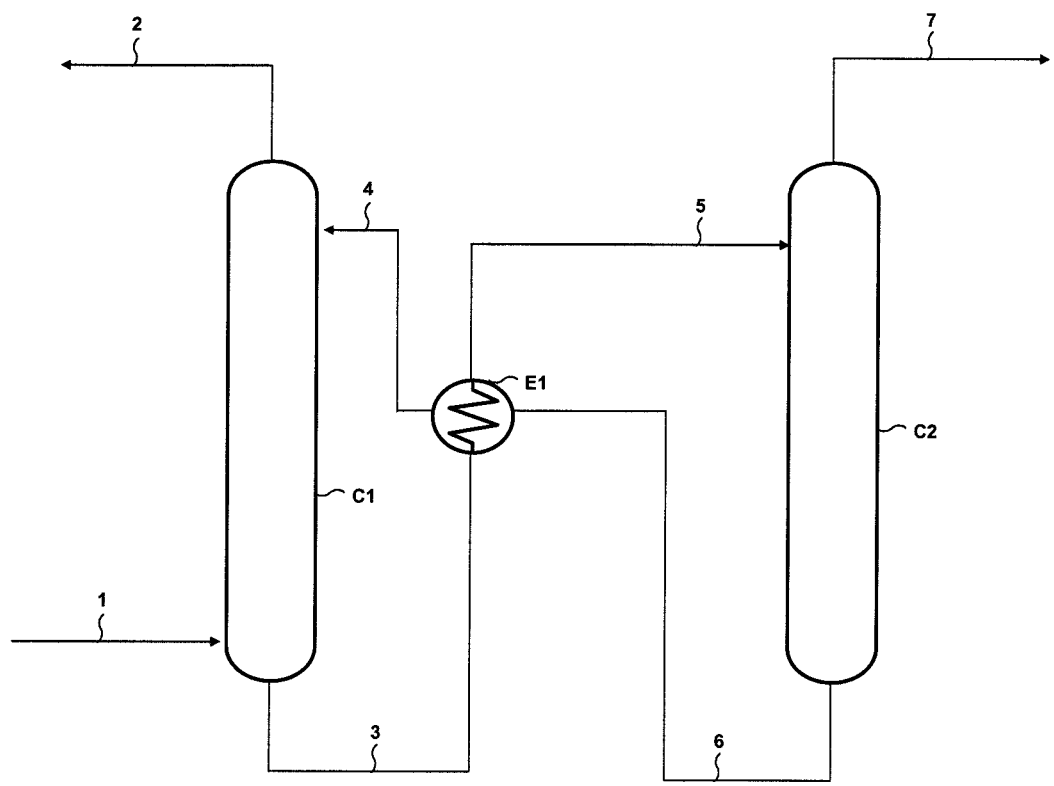
FIG. 1 is a flow sheet of an acid gas effluent treating method.

The present invention aims to remove the acid compounds of a gaseous effluent by using the combination of two types of amine compounds in aqueous solution.

The absorbent solution is a TMHDA-based aqueous solution which has the property of reacting reversibly with acid compounds such as $H_2S$ and $CO_2$. TMHDA in aqueous phase has the property of forming two separable liquid phases when it has absorbed a predetermined amount of acid compounds such as $CO_2$. In other words, the TMHDA aqueous solution forms two liquid phases when its loading (number of moles of acid compound captured per mole of amine of the absorbent solution) exceeds a critical demixing loading value, i.e. a loading threshold. Upon contacting in the absorption column, the loading of the absorbent solution increases as the acid compounds contained in the gas are absorbed. When feeding the TMHDA aqueous solution into the absorption column, the solution is a single-phase solution. In the absorption column, the loading of the absorbent solution might exceed the critical demixing loading value and the absorbent solution is therefore likely to divide into two phases. In form of two separate phases, the stream of acid compounds transferred from the gas to the solution would be highly impacted and the column height would have to be adjusted accordingly. This phenomenon therefore poses serious implementation problems and, considering the complexity of the system, it is difficult to model. In order to maintain the absorbent solution in single-phase form in the absorption column, the present invention aims to mix the TMHDA with specific activators which have the property of eliminating the demixing phenomenon by raising the $CO_2$ loading.

The composition of the absorbent solution according to the invention is given in detail hereafter.

Aqueous compositions based on N,N,N',N'-tetramethylhexane-1,6-diamine, or TMHDA, activated by a primary or secondary amine of formula (II) or (III) are of interest as absorbent solutions in all the acid gas (natural gas, combustion fumes, etc.) treating methods.

The N,N,N',N'-tetramethylhexane-1,6-diamine molecule has a higher absorption capacity with acid gases ($H_2S$, $CO_2$, COS, $SO_2$, $CS_2$ and mercaptans) than the conventionally used alkanolamines. Indeed, N,N,N',N'-tetramethylhexane-1,6-diamine has the specific feature of having very high loading values ($\alpha = n_{acid\,gas}/n_{amine}$) at low acid gas partial pressures, in relation to the conventionally used alkanolamines. Adding some weight percents of a primary or secondary amine of formula (II) or (III) to a TMHDA aqueous solution modifies only very slightly the loadings obtained, in particular at a low acid gas partial pressure. Using an aqueous absorbent solution according to the invention thus allows to save on the investment cost and the operating cost of a deacidizing unit (gas treatment and $CO_2$ capture).

Furthermore, the N,N,N',N'-tetramethylhexane-1,6-diamine molecule is interesting for its resistance to degradation, notably thermal degradation. It is therefore possible to regenerate the solvent at a higher temperature and thus to obtain an acid gas at a higher pressure if it is of interest in the case of acid gas reinjection. This is particularly interesting in the case of post-combustion $CO_2$ capture where the acid gas has to be compressed prior to reinjection and sequestration. Adding some weight percents of a primary or secondary amine of formula (II) or (III) does not change this conclusion because, considering its low concentration, the degradation rate of this molecule is very slow. Besides, primary amines of formula (II) or (III) are also interesting for their resistance to degradation. Using an aqueous absorbent solution according to the invention allows to save on the operating cost of the deacidizing unit, and on the investment cost and the operating cost linked with acid gas compression.

Furthermore, a specific feature of aqueous solutions of N,N,N',N'-tetramethylhexane-1,6-diamine or TMHDA activated by a primary or secondary amine of formula (II) or (III) is that they can be used in a deacidizing process with fractionated regeneration by heating as described in document FR-2,898,284.

Synthesis of N,N,N',N'-tetramethylhexane-1,6-diamine

N,N,N',N'-tetramethylhexane-1,6-diamine can be prepared according to various synthesis paths known to the person skilled in the art, described for example in the following documents: JP 1998-341556, EP 1998-105636, JP 1994-286224, JP 1993-25241, EP 1993-118476, EP 1988-309343, JP 1986-124298, JP 1985-147734, DE 1985-3523074, JP 1983-238221, and JP 1983-234589.

The reactions described in these documents are generally catalytic, with various catalyst compositions, for example: Pt, Pd, Rh, Ru, Cu, Ni, Co. Some of these paths identified from basic chemical products are represented below, (Cat.) designating in a generic manner the use of a catalyst.

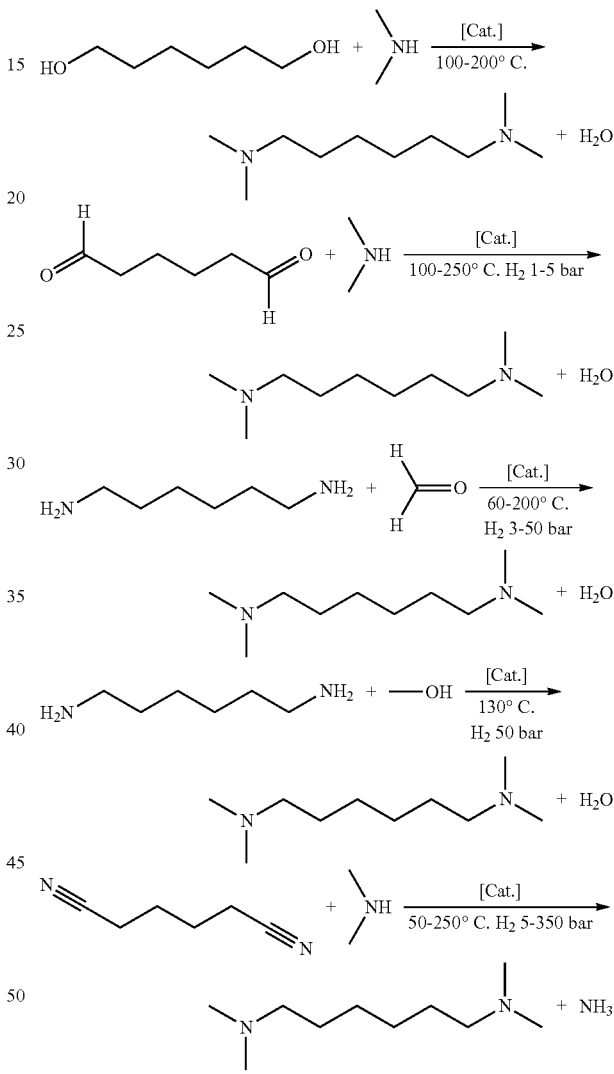

Nature of the Gaseous Effluents

The absorbent solutions according to the invention can be used to deacidize the following gaseous effluents: natural gas, syngas, combustion fumes, refinery gas, Claus tail gas, biomass fermentation gas, cement plant gas and incinerator fumes. These gaseous effluents contain one or more of the following acid compounds: $CO_2$, $H_2S$, mercaptans, COS, $CS_2$.

Combustion fumes are produced notably by the combustion of hydrocarbons, biogas, coal in a boiler or for a combustion gas turbine, for example in order to produce electricity. These fumes are at a temperature ranging between 20° C. and 60° C., at a pressure ranging between 1 and 5 bars, and they can comprise between 50 and 80% nitrogen, between 5 and 40% carbon dioxide, between 1 and 20% oxygen, and some impurities such as SOx and NOx if they have not been removed downstream of the deacidizing process.

Natural gas predominantly consists of gaseous hydrocarbons, but it can contain some of the following acid compounds: $CO_2$, $H_2S$, mercaptans, COS, $CS_2$. The proportion of these acid compounds is very variable and it can reach up to 40% for $CO_2$ and $H_2S$. The temperature of the natural gas can range between 20° C. and 100° C. The pressure of the natural gas to be treated can range between 10 and 120 bars.

Composition of the Absorbent Aqueous Solution

N,N,N',N'-tetramethylhexane-1,6-diamine can be in variable concentrations, ranging for example between 10 and 90 wt. %, preferably between 20 and 60 wt %, more preferably between 30 and 50 wt. % in the aqueous solution.

The compounds of general formula (II) or (III) have a non-zero concentration, for example below 50 wt. %, or even 30 wt. %, preferably below 20 wt. %, more preferably below 10 wt. % in the aqueous solution.

A non-exhaustive list of compounds of general formula (II) is given below:
BenzylAmine,
N-MethylBenzylAmine,
N-EthylBenzylAmine,
α-MethylBenzylAmine,
α-EthylBenzylAmine,
PhenethylAmine,
TetraHydroIsoQuinoline
IsoIndoline.

A non-exhaustive list of compounds of general formula (III) is given below:
ButylAmine,
N-Butylpiperazine.

The absorbent solution can contain at least 10 wt % water, generally between 10 and 90 wt. % water, more preferably at least 50 wt. %, for example between 60 and 70 wt. % water.

In a preferred embodiment, the absorbent solution according to the invention contains 62 to 68 wt. % water, 32 to 38 wt. % amines comprising N,N,N',N'-tetramethylhexane-1,6-diamine in admixture with at least one primary or secondary amine of formula (II) or (III) as the activator, the activator representing between 1 and 10 wt. % of the final absorbent solution.

This type of formulation is particularly interesting in case of $CO_2$ capture in industrial fumes or for treatment of natural gas containing $CO_2$ above the desired specification. Indeed, for this type of applications, one wants to increase the $CO_2$ capture kinetics in order to reduce the absorption column height.

In an embodiment, the absorbent solution based on N,N,N',N'-tetramethylhexane-1,6-diamine activated by a primary or secondary amine of formula (II) or (III) can comprise other organic compounds. Thus, the absorbent solution according to the invention can contain organic compounds non reactive towards the acid compounds (commonly referred to as physical solvents), which allow to increase the solubility of at least one or more acid compounds of the gaseous effluent. For example, the absorbent solution can comprise between 5 and 50 wt. % physical solvent such as alcohols, glycol ethers, lactames, N-alkylated pyrrolidones, N-alkylated piperidones, cyclotetramethylenesulfone, N-alkylformamides, N-alkylacetamides, ether-ketones or alkyl phosphates and derivatives thereof. By way of non-limitative example, it can be methanol, tetraethyleneglycoldimethylether, sulfolane or N-formyl morpholine.

In an embodiment, the absorbent solution based on N,N,N',N'-tetramethylhexane-1,6-diamine activated by a primary or secondary amine of formula (II) or (III) can comprise an organic or inorganic acid. A non-exhaustive list of acid compounds that can be used is given below:
formic acid
oxalic acid
acetic acid
propanoic acid
butanoic acid
amino-acid (glycine, taurine, etc.)
phosphoric acid
phosphorous acid
pyrophosphoric acid
sulfuric acid
sulfurous acid
nitrous acid
hydrochloric acid.

Method of Removing the Acid Compounds from a Gaseous Effluent (FIG. 1)

The implementation of an absorbent solution for deacidizing a gaseous effluent is achieved schematically by carrying out an absorption stage, followed by a regeneration stage. The absorption stage consists in contacting the gaseous effluent containing the acid compounds to be removed with the absorbent solution in an absorption column C1. The gaseous effluent to be treated (~0.1) and the absorbent solution (~0.4) are fed into column C1. Upon contacting, the organic compounds provided with an amine function of the absorbent solution (~4) react with the acid compounds contained in the effluent (~1) so as to obtain a gaseous effluent depleted in acid compounds (~2) that leaves the top of column C1 and an absorbent solution enriched in acid compounds (~3) that leaves the bottom of column C1. The absorbent solution enriched in acid compounds (~3) is sent to an exchanger E1 where it is heated by stream (~0.6) coming from regeneration column C2. The absorbent solution laden with acid compounds and heated at the outlet of exchanger E1 (~5) is fed into distillation column (or regeneration column) C2 where regeneration of the absorbent solution laden with acid compounds takes place. The regeneration stage thus notably consists in heating and possibly in expanding the absorbent solution enriched in acid compounds in order to release the acid compounds that leave the top of column C2 in gas form (~7). The regenerated absorbent solution, i.e. depleted in acid compounds (~6), leaves the bottom of column C2 and flows into exchanger E1 where it yields heat to stream (~3) as described above. The regenerated and cooled absorbent solution (~4) is then recycled to absorption column C1.

The acid compound absorption stage can be carried out at a pressure ranging between 1 and 120 bars, preferably between 20 and 100 bars for treating a natural gas, preferably between 1 and 3 bars for treating industrial fumes, and at a temperature ranging between 20° C. and 100° C., preferably between 30° C. and 90° C., more preferably between 30° C. and 60° C. In fact, the method according to the invention involves an excellent acid compound absorption capacity when the temperature in absorption column C1 ranges between 30° C. and 60° C.

The regeneration stage of the method according to the invention can be carried out by thermal regeneration, optionally complemented by one or more expansion stages.

Considering the high stability of N,N,N',N'-tetramethylhexane-1,6-diamine, it is possible to regenerate the absorbent solution according to the invention at high temperature in a distillation column. In general, the thermal regeneration stage is performed at a temperature ranging between 100° C. and 180° C., preferably between 130° C. and 170° C., and at a pressure ranging between 1 and 10 bars. Preferably, regeneration in the distillation column is conducted at a temperature ranging between 155° C. and 165° C., and at a pressure ranging between 6 and 8.5 bars in cases where one wants to reinject the acid gases. Regeneration in the distillation column is preferably carried out at a temperature ranging between 115° C. and 130° C. and at a pressure ranging between 1.7 and 3 bars in cases where the acid gas is sent to the atmosphere or to a downstream treating process such as a Claus process or a tail gas treating process.

Moreover, a demixing phenomenon for a given absorbent solution (liquid-liquid phase separation within the absorbent solution) can be induced by a temperature rise. Said demixing phenomenon can be controlled by selecting the operating conditions of the method and/or the composition of the absorbent solution. In this case, variants (FIG. 2) of the method according to the invention can be used, notably fractionated regeneration by heating the absorbent solution.

Figure 2:
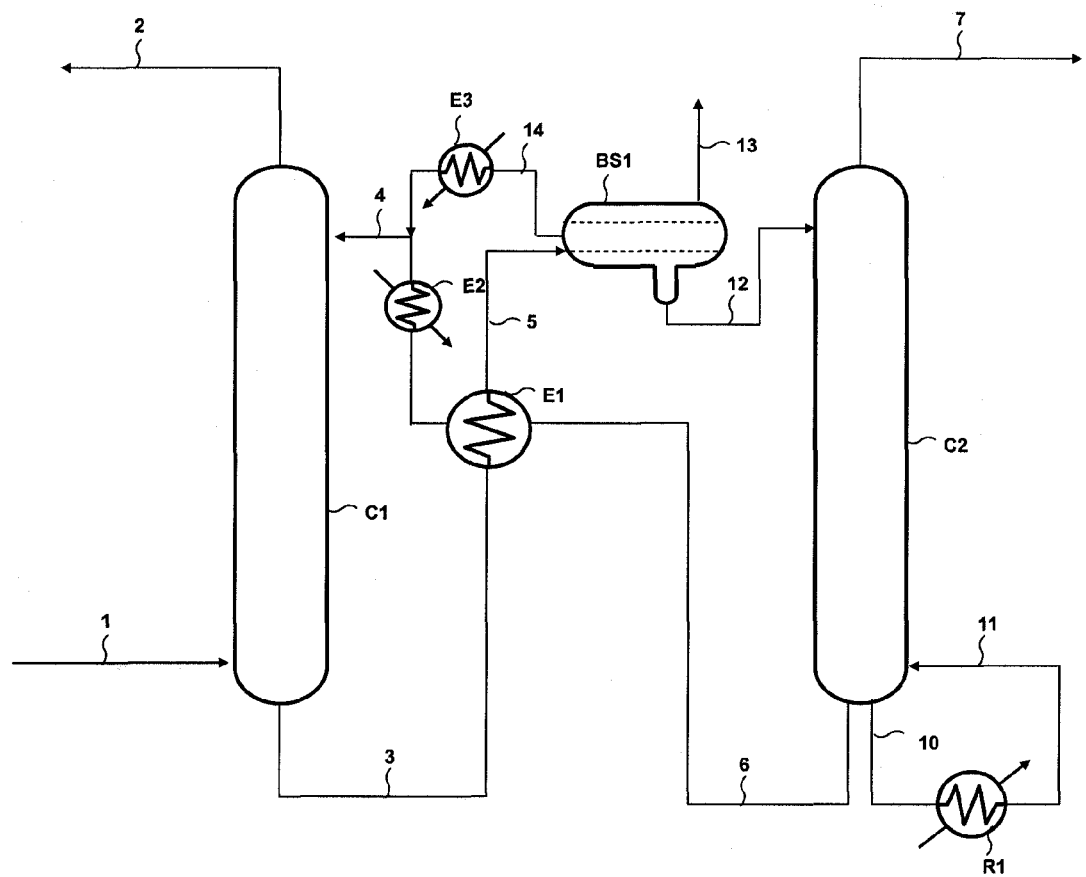
FIG. 2 is a flow sheet of an acid gas effluent treating method with fractionated regeneration through heating.

Method of Removing the Acid Compounds from a Gaseous Effluent with Fractionated Regeneration Through Heating (FIG. 2)

The implementation of an absorbent solution for deacidizing a gaseous effluent is achieved schematically by carrying out an absorption stage, followed by an absorbent solution heating stage, followed by an absorbent solution liquid-liquid separation stage, followed by a regeneration stage. The absorption stage consists in contacting the gaseous effluent containing the acid compounds to be removed with the absorbent solution in an absorption column C1. The gaseous effluent to be treated (~0.1) and the absorbent solution (~4) are fed into column C1. Upon contacting, the organic compounds provided with an amine function of the absorbent solution (~4) react with the acid compounds contained in the effluent (~1) so as to obtain a gaseous effluent depleted in acid compounds (~2) that leaves the top of column C1 and an absorbent solution enriched in acid compounds (~3) that leaves the bottom of column C1. The heating stage consists in raising the temperature of absorbent solution (~3) by passing for example into a thermal exchanger E1 so as to obtain a two-phase solution (~5). Two-phase solution (~5) is sent to a decanter BS1 where the liquid-liquid separation stage is carried out, which consists in separating the two phases obtained in the heating stage by sending the acid gas-rich phase (~12) to regeneration column C2 and by sending the acid gas-poor phase (~14) to absorption column C1, optionally after passage through an exchanger E3.

The gas phase released by heating absorbent solution (~3) in exchanger E1 is separated from the liquid phases in BS1 and discharged through line (~13).

The regeneration stage thus notably consists in heating in distillation column C2, and possibly in expanding, the absorbent solution enriched in acid compounds (~0.12) in order to release the acid compounds that leave the top of column C2 in gas form (~0.7). The regenerated absorbent solution, i.e. depleted in acid compounds (~6), leaves the bottom of column C2 and flows into exchanger E1 where it yields heat to stream (~3) as described above. The regenerated and cooled absorbent solution (~4) is then recycled to absorption column C1, optionally after passage through a new exchanger E2. In the bottom of distillation column C2, a portion of the absorbent solution is taken through line (~10), heated in reboiler R1 and fed again into the bottom of column C2 through line (~11).

The acid compound absorption stage can be carried out at a pressure ranging between 1 and 120 bars, preferably between 20 and 100 bars for treating a natural gas, preferably between 1 and 3 bars for treating industrial fumes, and at a temperature ranging between 20° C. and 100° C., preferably between 30° C. and 90° C., more preferably between 30° C. and 60° C. In fact, the method according to the invention involves an excellent acid compound absorption capacity when the temperature in absorption column C1 ranges between 30° C. and 60° C.

The regeneration stage of the method according to the invention can be carried out by thermal regeneration, optionally complemented by one or more expansion stages.

Considering the high stability of N,N,N',N'-tetramethyl-hexane-1,6-diamine, it is possible to regenerate the absorbent solution according to the invention at high temperature in a distillation column. In general, the thermal regeneration stage is performed at a temperature ranging between 100° C. and 180° C., and at a pressure ranging between 1 and 10 bars. Preferably, regeneration in the distillation column is conducted at a temperature ranging between 155° C. and 165° C., and at a pressure ranging between 6 and 8.5 bars in cases where it is desired to reinject the acid gases. Regeneration in the distillation column is preferably carried out at a temperature ranging between 115° C. and 130° C. and at a pressure ranging between 1.7 and 3 bars in cases where the acid gas is sent to the atmosphere or to a downstream treating process such as a Claus process or a tail gas treating process.

EXAMPLES

Aqueous solutions of N,N,N',N'-tetramethylhexane-1,6-diamine are used as absorbent solutions in these examples in combination with a compound of general formula (II) or (III). The compounds of general formula (II) used are, by way of example, TetraHydroIsoQuinoline (THIQ) and N-Methyl-BenzylAmine (N-MetBzA). The compounds of general formula (III) used are, by way of example, N-Butylpiperazine (N-ButPz) and n-butylamine.

| Formulation A | TMHDA + THIQ + $H_2O$ |
|---|---|
| Formulation B | TMHDA + N-MetBzA + $H_2O$ |
| Formulation C | TMHDA + N-ButPz + $H_2O$ |
| Formulation D | TMHDA + n-butylamine + $H_2O$ |

We first show that the physico-chemical properties of formulations A, B, C and D (i.e. liquid-liquid equilibrium) are very different from those of aqueous solutions of N,N,N',N'-tetramethylhexane-1,6-diamine or those of aqueous solutions of N,N,N',N'-tetramethylhexane-1,6-diamine in combination with a primary or secondary amine that does not meet general formula (II) or (III). These compounds selected by way of illustration are piperazine (Pz), 3-MethylAminoPropaneAmine (MAPA), DiEthanolAmine (DEA) and MonoEthanolAmine (MEA).

| Formulation E | TMHDA + $H_2O$ |
|---|---|
| Formulation F | TMHDA + Pz + $H_2O$ |
| Formulation G | TMHDA + MAPA + $H_2O$ |
| Formulation H | TMHDA + DEA + $H_2O$ |
| Formulation I | TMHDA + MEA + $H_2O$ |

We then show that the performances of formulations A, B and C (i.e. capture capacity, stability) are substantially equivalent to those of a 35 wt. % aqueous solution of TMHDA (i.e. formulation E).

Their performances are then compared with those of a 30 wt. % aqueous solution of MonoEthanolAmine, which is the reference solvent for a post-combustion fumes capture application, and with those of a 40 wt. % aqueous solution of Methyl DiEthanolAmine, which is the reference solvent for a natural gas treatment application.

Finally, their performances (i.e. capture capacity, stability) are compared with those of a 35% aqueous solution of N,N,N',N'-Tetramethylpropane-1,3 diamine (TMPDA), another tertiary diamine whose structure resembles that of N,N,N',N'-tetramethylhexane-1,6-diamine, for a post-combustion fumes capture application.

Example 1

Liquid-Liquid Equilibrium

The demixing phenomenon can be controlled by the nature of the activator that is added to an aqueous solution of N,N,N',N'-tetramethylhexane-1,6-diamine.

Depending on the composition of the N,N,N',N'-tetramethylhexane-1,6-diamine-based absorbent solution and on the possible presence of a primary or secondary amine, the composition of the gas to be treated (i.e. $CO_2$ partial pressure) and the temperature of the absorbent solution, a liquid-liquid phase separation may occur (demixing phenomenon). Laboratory tests (in perfectly stirred gas-liquid reactors) allow to determine the conditions under which demixing occurs for a given formulation (i.e. concentration of the amines and of the water), at a given temperature, by progressively increasing the $CO_2$ partial pressure and therefore the $CO_2$ loading ($\alpha = n_{acid\ gas}/n_{amine}$) at equilibrium. Furthermore, when the solvent is a two-phase solvent, the two liquid phases can be withdrawn and analysed in order to determine their composition (chromatographic analysis, acid base or volumetric titration).

According to the results of these laboratory tests, the absorbent solution can be used in a deacidizing method or in a deacidizing method with fractionated regeneration through heating, as described in FIG. 2. An absorbent solution based on N,N,N',N'-tetramethylhexane-1,6-diamine activated by a compound of general formula (II) or (III) is particularly suited for this type of method because it allows to work on a single-phase basis under the operating conditions corresponding to those of the absorber (i.e. generally 40° C.) and on a two-phase basis beyond the feed/effluent exchanger (i.e. generally 90° C.), and with a fast liquid-liquid phase separation.

1/ Liquid-Liquid Equilibrium at 40° C.

We deal here with liquid-liquid equilibria at 40° C., which corresponds to the low temperatures of an absorber. Three examples allow to highlight the importance of the structure of the activator, of the respective activator and TMHDA concentrations and of the total amine concentration.

1-A/ Activator Structure

We deal here with liquid-liquid equilibria at 40° C., which corresponds to the low temperatures of an absorber. The laboratory tests are carried out for formulations having a total amine concentration of 35 wt. %. The table hereafter sums up the results obtained for various formulations.

| Formulation | [TMHDA] (wt. %) | [Activator] (wt. %) | Loading where one enters the two-phase region | Loading where one exits the two-phase region |
|---|---|---|---|---|
| Formulation A | 30 | 5 | No demixing through loading increase for a $CO_2$ PP < 0.5 bar | |
| Formulation B | 30 | 5 | No demixing through loading increase for a $CO_2$ PP < 0.5 bar | |
| Formulation C | 30 | 5 | No demixing through loading increase for a $CO_2$ PP < 0.5 bar | |
| Formulation E | 35 | 0 | 0.54 | 1.50 |
| Formulation F | 30 | 5 | 0.64 | 0.78 |
| Formulation G | 30 | 5 | 0.44 | 0.87 |

It can be noted from the above table that a proportion of 5% of the activators of general formula (II) or (III) allows to totally eliminate the demixing phenomenon (formulations A, B and C) that is observed in the absence of an activator (formulation E). Formulations A, B and C above are therefore interesting because they allow to have a single-phase absorbent solution under the operating conditions corresponding to the absorber.

On the other hand, it can be seen that the activators that do not meet general formula (II) or (III) do not allow to totally eliminate the demixing phenomenon (formulations F and G).

1-B/ Activator Concentration

We deal here with liquid-liquid equilibria at 40° C., which corresponds to the low temperatures of an absorber. The laboratory tests are carried out for formulations of type A having a total amine concentration of 35 wt. %. The table hereafter sums up the results obtained for various TetraHydroIsoQuinoline concentrations.

| [THMDA] (wt. %) | [THIQ] (wt. %) | Loading where one enters the two-phase region | Loading where one exits the two-phase region |
|---|---|---|---|
| 35.0 | 0.0 | 0.54 | 1.50 |
| 34.0 | 1.0 | 0.77 | 1.45 |
| 32.5 | 2.5 | No demixing through loading increase for a $CO_2$ PP < 0.5 bar | |
| 30.0 | 5.0 | No demixing through loading increase for a $CO_2$ PP < 0.5 bar | |

The effect observed with the activators of general formula (II) or (III) is all the more surprising since a very small proportion of activator (i.e. less than 2.5 wt. %) such as TetraHydroIsoQuinoline (formulation A) allows to totally eliminate the demixing phenomenon that is observed in the absence of an activator (formulation E).

1-C/ Total Amine Concentration

We deal here with liquid-liquid equilibria at 40° C., which corresponds to the low temperatures of an absorber. The laboratory tests are carried out for formulations having a total amine concentration of 56 wt. %. The table hereafter sums up the results obtained for various formulations.

It can first be noted that the demixing phenomenon that is observed in the absence of an activator (formulation E) is all the more marked as the total amine concentration is high. For a total concentration of 35 wt. % (case described in example 1-A), one enters the two-phase region for a loading value of 0.54 and one exits this region for a loading value of 1.50. For a total concentration of 56 wt. % (case described in example 1-C), one enters the two-phase region for a loading value of 0.1 and it is difficult to determine the loading at which one exits the two-phase region with the equipments available.

| Formulation | [THDA] (wt. %) | [Activator] (wt. %) | Loading where one enters the two-phase region |
|---|---|---|---|
| Formulation B | 50 | 6 | No demixing through loading increase |
| Formulation D | 50 | 6 | No demixing through loading increase |
| Formulation E | 56 | 0 | 0.10 |
| Formulation H | 50 | 6 | 0.12 |
| Formulation I | 50 | 6 | 0.23 |

It can furthermore be noted from the above table that 6% of the activators of general formula (II) or (III) allow to totally eliminate the demixing phenomenon (formulations B and D) that is observed in the absence of an activator (formulation E). Formulations B and D are therefore interesting because they allow to have a single-phase absorbent solution under the operating conditions corresponding to the absorber.

On the other hand, it can be seen that the activators that do not meet general formula (II) or (III) do not allow to totally eliminate the demixing phenomenon (formulations H and I).

2/ Liquid-Liquid Equilibrium at 90° C.

We now deal with liquid-liquid equilibria at 90° C., which corresponds to the typical temperatures after passage through the feed/effluent exchanger in a deacidizing method.

Depending on the composition of the N,N,N',N'-tetramethylhexane-1,6-diamine-based absorbent solution and on the possible presence of a primary or secondary amine, the composition of the gas to be treated and the temperature of the absorbent solution, a liquid-liquid phase separation may occur (demixing phenomenon).

By way of illustration, we give hereafter the composition (i.e. concentration of the amines and loading=number of moles of acid gas captured to the number of moles of amine) of the lower and upper phases obtained for the formulations of type A, for example for a N,N,N',N'-tetramethylhexane-1,6-diamine concentration of 30 wt. % and a TetraHydroIsoQuinoline concentration of 5 wt. %, at 90° C., for various partial pressures of acid gas at equilibrium with the absorbent solution.

| CO2 PP (bar) | Phase | [TMHDA] (wt. %) | [THIQ] (wt. %) | [Amine] (wt. %) | Loading |
|---|---|---|---|---|---|
| 0 | Lower | 1.9 | 0.4 | 2.3 | 0 |
|   | Upper | 69.9 | 9.1 | 79.0 | 0 |
| 0.1 | Lower | 9.5 | 2.2 | 11.7 | 0.62 |
|   | Upper | 69.9 | 9.1 | 79.0 | 0.03 |
| 0.3 | Lower | 16.9 | 3.5 | 20.4 | 0.67 |
|   | Upper | 73.6 | 6.5 | 80.1 | 0.06 |
| 1 | Lower | 19.8 | 3.7 | 23.5 | 0.78 |
|   | Upper | 73.8 | 5.1 | 78.9 | 0.09 |

It can first be noted that the upper phases that are obtained for various $CO_2$ partial pressures have a very high amine concentration and very low loading values (below 0.1). Conversely, the lower phases that are obtained for various $CO_2$ partial pressures have a low to moderate amine concentration and high loading values. The higher the $CO_2$ partial pressure at equilibrium, the higher the amine concentration in the lower phase.

The phases that are obtained after passage through the feed/effluent exchanger can thus be separated, and the $CO_2$-poor phase (upper phase) can be directly recycled to the absorber, whereas the $CO_2$-rich phase (lower phase) has to be sent to a regeneration stage. This operation allows to reduce the solvent flow rate in the regenerator and thus to reduce the solvent regeneration energy.

Besides, it can be noted that the activator concentration is always higher in the upper phase than in the lower phase. This is another advantage of the formulations of type A since the concentration of the activator can be increased so as to increase the $CO_2$ capture kinetics without the latter penalizing the regeneration stage. Indeed, due to the liquid-liquid separation performed after the feed/effluent exchanger, part of the activator circulates in a loop in the absorber.

Example 2

Capture Capacity

1/ Impact of the Activator on the Capture Capacities

We deal here with the capture capacity of aqueous solutions of TMHDA activated by a primary or secondary amine of general formula (II) or (III). By way of example, the table below allows to compare the loadings ($\alpha = n_{acid\ gas}/n_{amine}$) obtained at 40° C. for various $CO_2$ partial pressures for a total amine concentration of 35%, without (formulation E) and with various activators of general formula (II) or (III) (formulations A, B and C).

| Formulation | [TMHDA] (wt. %) | [Activator] (wt. %) | T (° C.) | Loading $\alpha = n_{CO2}/n_{amine}$ | | |
|---|---|---|---|---|---|---|
| | | | | $PP_{CO2} =$ 0.1 bar | $PP_{CO2} =$ 0.3 bar | $PP_{CO2} =$ 1 bar |
| Formulation E | 35 | 0 | 40 | 1.18 | 1.68 | 1.88 |
| Formulation A | 30 | 5 | 40 | 1.12 | 1.44 | 1.55 |
| Formulation B | 30 | 5 | 40 | 1.29 | 1.52 | 1.67 |
| Formulation C | 30 | 5 | 40 | 1.25 | 1.55 | 1.71 |

It can be noted that the capture capacity of TMHDA is very poorly affected by the substitution of some weight percents of TMHDA for some weight percents of activator, notably at low $CO_2$ partial pressures.

For simplification reasons, we compare in the next paragraph only the properties of a 35 wt. % TMHDA aqueous solution (formulation E) with those of the amines commonly used for natural gas treatment and $CO_2$ capture applications.

2/ Comparison of the Capture Capacities with Other Absorbent Solutions

By way of example, we can compare the loadings ($\alpha = n_{acid\ gas}/n_{amine}$) obtained at 40° C. for various $CO_2$ partial pressures between a 35 wt. % TMHDA aqueous solution (formulation E) and a 30 wt. % MonoEthanolAmine and 35 wt. % TMPDA absorbent solution:

| Amine | Concentration | T (° C.) | Loading $\alpha = n_{CO2}/n_{amine}$ | | |
|---|---|---|---|---|---|
| | | | $PP_{CO2} =$ 0.1 bar | $PP_{CO2} =$ 0.3 bar | $PP_{CO2} =$ 1 bar |
| TMHDA | 35 wt. % | 40 | 1.18 | 1.68 | 1.88 |
| TMPDA | 35 wt. % | 40 | 0.86 | 1.13 | 1.51 |
| MEA | 30 wt. % | 40 | 0.52 | 0.55 | 0.6 |

By way of example, we can compare the loadings ($\alpha = n_{acid\ gas}/n_{amine}$) obtained at 40° C. for various $H_2S$ partial pressures between a 35 wt. % TMHDA aqueous solution (formulation E) and a 40 wt. % MethylDiEthanolAmine absorbent solution:

| Amine | Concentration | T (° C.) | Loading α = $n_{H2S}/n_{amine}$ | | |
|---|---|---|---|---|---|
| | | | $PP_{H2S}$ = 0.01 bar | $PP_{H2S}$ = 0.03 bar | $PP_{H2S}$ = 0.1 bar |
| TMHDA | 35 wt. % | 40 | 0.55 | 0.98 | 1.76 |
| MDEA | 40 wt. % | 40 | 0.11 | 0.20 | 0.37 |

3/ Conclusion

These examples show the high loading values that can be obtained by means of aqueous solutions of TMHDA activated by a primary or secondary amine of general formula (II) or (III), notably for low acid gas partial pressures.

Example 3

Stability

The N,N,N',N'-tetramethylhexane-1,6-diamine molecule has the specific feature of being very resistant to the degradations that may occur in a deacidizing unit.

The activators of general formula (II) or (III) also have the specific feature of being very resistant to the degradations that may occur in a deacidizing unit.

On the laboratory scale, aqueous amine solutions can be degraded within closed reactors, heated to a temperature T, and brought under pressure with a partial pressure PP of different gases ($CO_2$, $O_2$, $H_2S$, $N_2$). The liquid phase is stirred by means of a bar magnet. After a given time, a sample of the liquid phase can be taken and analysed using various techniques, notably gas chromatography. The table below gives the degradation rate TD of the absorbent solution, under various conditions, for a 15-day duration, defined by the equation below:

$$TD(\%) = \frac{[Amine] - [Amine]°}{[Amine]°}$$

where (Amine) is the amine concentration in the degraded sample and (Amine) is the amine concentration in the non-degraded solution.

The lower the degradation rate TD, all other things being equal, the more the amine can be considered to be stable.

For a formulation comprising TMHDA and an activator of general formula (II) or (III), the concentration of the activators can be very low (for example 2.5 wt. %, see Example 1 Section 1-B). Besides, in case of an implementation of the method with fractionated regeneration through heating, a large part of the activator circulates in a loop in the absorber (see Example 1 Section 2). Thus, the activator concentration in the regenerator, where the major part of the degradation reactions occur due to high temperatures, can be extremely low. These arguments converge towards the fact that these activators will undergo a poor degradation in the absorption method according to the invention.

Considering that the degradation tests are carried out under very severe conditions, many degradation products can be generated. When conducting a degradation test on a TMHDA formulation activated by some weight percents of a primary or secondary amine, it is therefore very diffcult to quantify with certainty the degradation rate of the activator. Consequently, the stability of the activator alone is tested during an independent series of test runs.

We first give the results obtained for TMHDA alone, then for the activators of general formula (II) alone.

1/ TMHDA Stability

The table below gives the degradation rate TD of various amine aqueous solutions, for a temperature of 140° C., in the absence and in the presence of different acid gases.

| Amine | Concentration | T (° C.) | Degradation rate | | | |
|---|---|---|---|---|---|---|
| | | | Solvent vapour pressure | $PP_{CO2}$ = 20 bar | $PP_{CO2}$ = 4.2 bar | $PP_{CO2}$ = 16.6 bar + $PP_{H2S}$ = 3.4 bar |
| TMHDA | 35 wt. % | 140 | 0% | <3% | 5% | <3% |
| TMPDA | 35 wt. % | 140 | 6.7% | 21% | 12% | — |
| MDEA | 40 wt. % | 140 | 0% | 25% | 14% | 29% |
| MEA | 30 wt. % | 140 | 5.4% | 42% | 21% | — |

The table below gives the degradation rate TD of various amine aqueous solutions, for a temperature of 180° C., in the absence and in the presence of acid gas, which is representative of the degradations that might occur in the regenerator bottom if it is desired to obtain an acid gas at high pressure for reinjection applications.

| Amine | Concentration | T (° C.) | Degradation rate | |
|---|---|---|---|---|
| | | | Solvent vapour pressure | $PP_{CO2}$ = 20 bar |
| TMHDA | 35 wt. % | 180 | 5% | 5% |
| MDEA | 40 wt. % | 180 | 26% | 77% |

This example shows that using an absorbent solution predominantly made up of N,N,N',N'-tetramethylhexane-1,6-diamine allows to obtain a low degradation rate in relation to the amine-based absorbent solutions of the prior art (MethylDiEthanolAmine and MonoEthanolAmine). It can furthermore be observed that it is much more stable than a molecule of very close structure such as N,N,N',N'-TetraMethylPropane-1,3-diamine (TMPDA).

2/ Stability of the Activators of General Formula (II)

The table below gives the degradation rate TD of various aqueous activator solutions, such as TetraHydroIsoQuinoline and N-MethylBenzylamine meeting general formula (II), and of various aqueous activator solutions known to the person skilled in the art, for a temperature of 140° C. on the one hand in the presence of $CO_2$ and on the other hand in the presence of $O_2$.

| Amine | Concentration | T (° C.) | Degradation rate | |
|---|---|---|---|---|
| | | | $PP_{CO2}$ = 20 bar | $PP_{O2}$ = 4.2 bar |
| THIQ | 4M | 140 | 5% | 10% |
| N-MBzA | 4M | 140 | 11% | 9% |
| DEA | 4M | 140 | 93% | 22% |
| MEA | 4M | 140 | 42% | 21% |

This example shows that using primary or secondary amines meeting general formula (II) allows to obtain a low degradation rate in relation to activators of the prior art (Di-EthanolAmine and MonoEthanolAmine), in the presence of $CO_2$, but also in the presence of oxygen contained, for example, in combustion fumes.

3/ Conclusion

It is therefore possible to regenerate the absorbent solution according to the invention at a higher temperature and thus to obtain an acid gas at a higher pressure. This is particularly interesting in the case of post-combustion $CO_2$ capture where the acid gas has to be compressed in order to be liquefied prior to reinjection.

The invention claimed is:

1. A method for removing the acid compounds contained in a gaseous effluent, comprising:

carrying out an acid compound absorption stage comprising contacting the effluent with an absorbent solution comprising water and at least one amine of formula (I) (N,N,N',N'-tetramethylhexane-1,6-diamine)

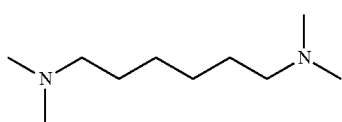
(I)

and controlling a demixing phenomenon of the absorbent solution by adding at least one activating compound selected from the group consisting of ButylAmine, N-Butylpiperazine and a primary or secondary amine meeting formula (II), formula (II) being:

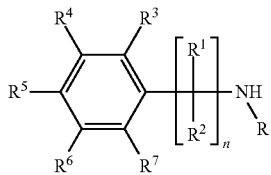

wherein
n=1 or 2, and
each group R1, R2, R3, R4, R5, R6, R7 and R is selected independently among one of the elements selected from the group consisting of: a hydrogen atom, and an alkyl group with 1 to 2 carbon atoms, group R is not linked to any one of groups R1 to R7, and group R is linked by R3 or R7 to the aromatic ring of formula (II) so as to form a heterocycle with 5 to 6 atoms, so as to obtain a gaseous effluent depleted in acid compounds and a single-phase absorbent solution laden with acid compounds in an absorption column, and
then carrying out a regeneration stage comprising sending at least part of the solution laden with acid compounds to a distillation column in order to release the acid compounds in form of a gaseous effluent and to obtain a regenerated absorbent solution.

2. A method as claimed in claim 1, wherein the acid compound absorption stage is carried out at a pressure ranging between 1 and 120 bars, and at a temperature ranging between 30° C. and 100° C.

3. A method as claimed in claim 2, wherein the acid compound absorption stage is carried out at a temperature ranging between 30° C. and 60° C.

4. A method as claimed in claim 1, wherein the regeneration stage is carried out at a pressure ranging between 1 and 10 bars, and at a temperature ranging between 100° C. and 180° C.

5. A method as claimed in claim 1, wherein a first stage of expansion of the absorbent solution laden with acid compounds is carried out prior to the regeneration stage.

6. A method as claimed in claim 1, wherein the absorption stage is followed by at least one liquid-liquid separation stage by heating the absorbent solution laden with acid compounds, then by at least one stage of regeneration of the absorbent solution laden with acid compounds.

7. A method for treating natural gas as claimed in claim 1.

8. A method for treating gases of industrial origin as claimed in claim 1.

9. A method for treating gases of industrial origin as claimed in claim 8 for $CO_2$ capture.

10. A method as claimed in claim 1, wherein the at least one activating compound is selected from the group consisting of:
BenzylAmine
α-MethylBenzylAmine
α-EthylBenzylAmine
PhenethylAmine
TetraHydroIsoQuinoline and
IsoIndoline.

11. A method as claimed in claim 1, wherein the at least one activating compound is BenzylAmine.

12. A method as claimed in claim 1, wherein the at least one activating compound is selected from the group consisting of:
α-MethylBenzylAmine
α-EthylBenzylAmine
PhenethylAmine
TetraHydroIsoQuinoline and
IsoIndoline.

13. A method as claimed in claim 1, wherein the at least one activating compound is selected from the group consisting of:
α-MethylBenzylAmine
α-EthylBenzylAmine
PhenethylAmine and
IsoIndoline.

* * * * *